United States Patent [19]

Secrist, III et al.

[11] Patent Number: 4,985,433

[45] Date of Patent: Jan. 15, 1991

[54] 2-AMINO-7-(PYRIDINYLMETHYL)-3H,5H-PYRROLO[3,2-D]PYRIMIDIN-4-ONES AND PHARMACEUTICAL USES AND COMPOSITIONS CONTAINING THE SAME

[75] Inventors: John A. Secrist, III; John A. Montgomery; Steve E. Ealick, all of Birmingham, Ala.; Mark D. Erion, Livingston; Wayne C. Guida, Fanwood, both of N.J.

[73] Assignee: BioCryst, Inc., Birmingham, Ala.

[21] Appl. No.: 429,100

[22] Filed: Oct. 31, 1989

[51] Int. Cl.$^5$ .................. A61K 31/505; C07D 487/00
[52] U.S. Cl. ..................................... 514/258; 544/280
[58] Field of Search .......................... 544/280; 574/258

[56] References Cited

U.S. PATENT DOCUMENTS 4,921,858  5/1990  Malone et al. ....................... 544/280
4,923,872  5/1990  Kostlan et al. ...................... 544/280

OTHER PUBLICATIONS

M. I. Lim et al., J. Org. Chem. 44, 3826 (1979).
M. I. Lim et al., Tetrahedron Lett. 21, 1013 (1980).
M. I. Lim et al., Tetrahedron Lett. 22, 25 (1981).
M. I. Lim et al., J. Org. Chem. 48, 780 (1983).

*Primary Examiner*—Cecilia Shen
*Attorney, Agent, or Firm*—Wegner, Cantor, Mueller & Player

[57] ABSTRACT

Disclosed is a compound containing a 2-amino-7-(substituted methyl)-3H,5H-pyrrolo[3,2-d]pyrimidin-4-one wherein substituted methyl is —CH$_2$—R wherein R is optionally substituted pyridinyl, a pharmaceutical composition containing the compound, and a method for the selective suppression of mammalian T-cell function without diminished effect on humoral immunity which involves administering the composition to a mammal.

9 Claims, No Drawings

2-AMINO-7-(PYRIDINYLMETHYL)-3H,5H-PYRROLO[3,2-D]PYRIMIDIN-4-ONES AND PHARMACEUTICAL USES AND COMPOSITIONS CONTAINING THE SAME

The present invention relates to derivatives of 2-amino-3H,5H-pyrrolo[3,2-d]pyrimidin-4-one.

Purine nucleoside phosphorylase (PNP) catalyzes the phosphorolysis of purine nucleosides in a reversible reaction. Individuals who are deficient in PNP exhibit impaired T-cell development, resulting in lowered cell-mediated immunity, but normal B-cell development, resulting in normal humoral immunity. Accordingly, specific inhibitors of PNP that selectively inhibit T-cell development without damaging humoral immunity could be potentially effective against disorders in which activated T-cells are pathogenic.

Accordingly, the present invention is a PNP inhibitor that is a derivative of 2-amino-7-methyl-3H,5H-pyrrolo[3,2-d]pyrimidin-4-one.

In a first aspect of the invention there is provided a compound 2-amino-7-(substituted methyl)-3H,5H-pyrrolo[3,2-d]-pyrimidin-4-one (I) wherein substituted methyl is

—CH$_2$-R.

The R group is optionally substituted pyridinyl. In a preferred aspect, R is unsubstituted, i.e., the compound (I) is 2-amino-7-(3-pyridinylmethyl)-3H,5H-pyrrolo[3,2-d]pyrimidin-4-one (IA), 2-amino-7-(2-pyridinylmethyl)-3H,5H-pyrrolo[3,2-d]-pyrimidin-4-one (IB), or 2-amino-7-(4-pyridinylmethyl)-3H,5H-pyrrolo[3,2-d]-pyrimidin-4-one (IC). In an alternative preferred embodiment the R has one or two substituents selected from the group consisting of halogen, hydroxy, alkoxy, alkyl, or trifluoromethyl. As halogen is preferably mentioned chloro or fluoro. As alkoxy is preferably mentioned lower alkoxy, including methoxy, ethoxy, propoxy and butoxy. As alkyl is preferably mentioned lower alkyl, including methyl, ethyl, propyl and butyl.

In a second aspect of the invention there is provided a method for the selective suppression of mammalian T-cell function without diminished effect on humoral immunity which comprises administering to a mammal the compound (I), whereby said compound inhibits purine nucleoside phosphorylase and thereby T-cell formation.

In a further aspect of the present invention there is provided a pharmaceutical composition for the selective suppression of mammalian T-cell function without diminished effect on humoral immunity which comprises an effective amount of the compound (I) and a pharmaceutically acceptable diluent therefor.

The invention further relates to pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with (a) diluents, e.g., lactose, dextrose, sucrose, mannitol, sorbitol, cellulose and/or glycine; (b) lubricants, e.g., silica, talcum, stearic acid, its magnesium or calcium salt and/or polyethyleneglycol; for tablets also (c) binders, e.g., magnesium aluminum silicate, starch paste, gelatin, tragacanth, methylcellulose, sodium carboxymethylcellulose and/or polyvinylpyrrolidone; if desired (d) disintegrants, e.g., starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The present invention provides a method of inhibiting purine nucleoside phosphorylase activity in mammals and treating diseases and conditions responsive thereto, e.g., autoimmune disorders, rejection of transplantation, or psoriasis, which comprises administering to a mammal in need thereof an effective amount of a compound of the invention or of a pharmaceutical composition comprising a said compound in combination with one or more pharmaceutically acceptable carriers.

A further aspect of the invention relates to a method of inhibiting the phosphorolysis and metabolic breakdown of antiviral or antitumor purinenucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g., of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2',3'-dideoxypurine nucleosides known in the art, e.g., of 2',3'-dideoxyinosine, 2',3'-dideoxyguanosine or 2'-3'-dideoxyadenoside for the treatment of retrovirus infections, e.g., HIV-retrovirus infections (acquired immunodeficiency syndrome, AIDS). 2',3'-Dideoxypurine nucleosides are known in the art as inhibitors of HIV retrovirus infectivity and to be metabolically degraded by PNP, e.g., as described in *Biochemical Pharmacology* 22, 3797 (1987). Such are administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

The pharmaceutical composition may be oral, parenteral, suppository or other form which delivers the compound (I) into the bloodstream of a mammal to be treated. An oral form has from about 1 to about 150 mg of the compound (I) for an adult (50 to 70 kg) which is mixed together with pharmaceutically acceptable diluents such as lactose. In a typical capsule, 25 mg of the compound (I) are mixed together with 192 mg lactose, 80 mg modified starch and 3 mg magnesium stearate. Injectable forms of the compound are also contemplated for administration.

The present invention is also useful with other therapeutic agents. A daily dosage for a human weighing 50 to 70 kg of 1–50 mg/kg inhibits metabolic destruction of certain anticancer agents such as beta-2'-deoxy-6-thioguanosine and antiviral agents such as 2',3'-dideoxyinosine, an anti-AIDS drug. These types of agents are known to be susceptible to cleavage. Upon cleavage, the agents lose effectiveness. The compounds of the present invention are capable of reducing such cleavage. This protection, therefore, enhances the efficacy of other chemotherapeutic agents.

One method of making the compound (I) of the present invention uses a 3-(pyridinyl)propionitrile as the starting material to make the compound (I). The appropriate 3-(pyridinyl)propionitrile can be produced by converting the corresponding 3-(pyridinyl)propionyl chloride to the corresponding amide by ammonolysis with, e.g., ammonium hydroxide, which is then dehydrated to the desired nitrile by distillation with a dehydrating agent, such as $POCl_3$ or $SOCl_2$. Alternatively, the starting material is produced by condensation of the 3-aldehyde with cyanoacetic acid followed by decarboxylation to give the corresponding substituted acrylonitrile, which is hydrogenated to give the corresponding 3-(pyridinyl)propionitrile by either catalytic hydrogenation or magnesium metal dissolving in methanol at 0° C., such as disclosed in Profitt, J., et al., *J. Org. Chem.*, 40, 127 (1975).

The compound (I) is then prepared from the starting material by an adaptation of the synthetic methodology disclosed in M. I. Lim, R. S. Klein, and J. J. Fox, *J. Org. Chem.*, 44. 3826 (1979); M. I. Lim, R. S. Klein, and J. J. Fox, *Tetrahedron Lett.*, 21, 1013 (1980); M. I. Lim and R. S. Klein, *Tetrahedron Lett.*, 22, 25 (1981); M. I. Lim, W. Y. Ren, B. A. Otter, and R. S. Klein, *J. Org. Chem.*, 48, 780 (1983).

In order to more fully describe the present invention the following non-limiting examples are provided. In the examples all parts and percentages are by weight unless indicated otherwise. Proportions of solvent mixtures used as chromatographic eluents are by volume.

EXAMPLE 1

3-(3-Pyridinyl)propionitrile is prepared in this example. A three-neck flask carrying a magnetic stir bar is fitted with a thermometer, pressure equalizing addition funnel, and a reflux condenser carrying an argon inlet. Freshly powdered potassium hydroxide (6.6 g, 0.1 mol) and anhydrous acetonitrile (150 ml) are charged into the flask and heated at reflux while 3-pyridinecarboxaldehyde (10.7 g, 0.1 mol) in anhydrous acetonitrile (50 ml) is added dropwise over a period of about five minutes and refluxing continued for about another three minutes. The resulting hot reaction mixture is poured into an ice/water mixture (100 g), and the resulting solution is extracted with $CH_2Cl_2$ (3×100 ml), dried with $Na_2SO_4$, and evaporated to give crude 3-(3-pyridinyl)acrylonitrile, which is purified by column chromatography over silica gel using $CHCl_3$ as the eluent; yield 3.3 g (25.6%).

Under an argon atmosphere, a stirred solution of the acrylonitrile (2.662 g, 0.02 mol) in 99% ethanol (100 ml) is treated with a drop of 4% aqueous sodium hydroxide followed by sodium borohydride (0.378 g, 0.01 mol). Additional sodium borohydride (0.378 g) is added twice more at four-hour intervals. The mixture is stirred at room temperature overnight, diluted with water, extracted with EtOAc and dried with $Na_2SO_4$. The solvent is removed under reduced pressure and the crude product obtained is chromatographed over a column of silica using chloroform/methanol (40/1) as the eluent to give 2.2 g (84.6%) of the product as a colorless oil.

EXAMPLE 2

3-(3-Pyridinyl)propionitrile of Example 1 is further treated in the synthesis of the present invention. Under an atmosphere of dry $N_2$, a mixture of 3-(3-pyridinyl)propionitrile (0.661 g, 5.0 mmole), sodium hydride (0.240 g, 10.0 mmole), and ethyl formate (1.11 g, 15.0 mmole) in anhydrous tetrahydrofuran (20 ml) is stirred for 48 hours with protection from air and moisture. Volatile matter is evaporated, and a solution of the solid residue in 15 ml of cold water is adjusted at 0° C. to a pH of 6 with cold 6N HCl. The resulting oily mixture is extracted with $CHCl_3$, and the extract is washed with water, dried using $Na_2SO_4$, and evaporated to give a dark oil, which is a mixture of 2-formyl-3-(3-pyridinyl)propionitrile and the nitrile starting material. This crude product is used in the next reaction without further purification.

EXAMPLE 3

Glycine methyl ester hydrochloride (0.942 g, 7.5 mmole) and anhydrous sodium acetate (0.615 g, 7.5 mmole) are added to a solution of the crude formyl compound (0.89 g) in $MeOH/H_2O$ (4:1, 50 ml). After 24 hours, the MeOH is evaporated in vacuo, and the mixture of water and oil is extracted with $CHCl_3$. The $CHCl_3$ layer is dried ($Na_2SO_4$) and evaporated to give an amber oil which is applied to a silica gel column. Elution with $CHCl_3$ gave two major bands: (1) 3-(3-pyridinyl)propionitrile (used as starting material in the previous step), and (2) the desired enamine.

EXAMPLE 4

Under a nitrogen atmosphere, ethyl chloroformate (0.521 g, 4.8 mmole) is added dropwise to a solution of the enamine of Example 3 (0.513 g, 3.2 mmole) and 1,5-diazabicyclo[4.3.0]non-5-ene (DBN, 1.37 g, 11.1 mmole) in dry CH$_2$Cl$_2$ (15 ml) with external cooling in an ice bath. After stirring at 0° C. for one hour, the solution is allowed to a stand at room temperature overnight. After checking progress by TLC, additional ClCO$_2$Et (0.1 ml) and DBN (1.0 ml) are added to complete the conversion, and the solution is allowed to stand for 24 hours. Volatile matter is evaporated in vacuo, and the viscous residue is purified on a short silica gel column (whose main purpose is to remove the less-mobile DBN) to give an N-blocked pyrrole, which is used for the next step without further purification.

EXAMPLE 5

To a solution of the N-blocked pyrrole of Example 4 (0.635 g, 2.0 mmole) in MeOH (50 ml) is added solid Na$_2$CO$_3$ (0.212 g, 2.0 mmole), and the reaction mixture is stirred at room temperature for 48 hr with separation of the resultant deblocked pyrrole. The mixture is evaporated to dryness, and the residue is triturated thoroughly with H$_2$O (25 ml) to dissolve inorganics and extracted with CHCl$_3$ (3×100 ml). The extract is dried (Na$_2$SO$_4$) and evaporated to give a viscous gum that crystallized upon drying in vacuo for use as an intermediate without further purification. More extensive purification can, however, be effected by using either column chromatography employing silica gel/CHCl$_3$ or recrystallization from toluene/cyclohexane (1:3).

EXAMPLE 6

Benzoyl isothiocyanate (0.232 g, 1.42 mmole) is added dropwise to a solution of the unblocked pyrrole of Example 5 (0.290 g, 1.18 mmole) in dry CH$_2$Cl$_2$ (100 ml). After 1 h at room temperature, the solution is evaporated, and the gummy residue is stirred in Et$_2$O/cyclohexane (1:1, 20 ml). The resulting suspension of yellow solid is filtered under N$_2$ pressure, and the thioureido product is dried in vacuo over P$_2$O$_5$.

EXAMPLE 7

Methyl iodide (0.228 g, 1.61 mmole) is added to a solution of the thioureido product of Example 6 (0.383 g, 0.94 mmole) and DBN (0.140 g, 1.12 mmole) in dry CH$_2$Cl$_2$ (10 ml) at 0° C. The solution is stirred at 0° C. for 15 min., at ambient temperature for 1 h, and then evaporated in vacuo. A solution of the residue in CHCl$_3$ is chromatographed on a silica gel column with CHCl$_3$/methanol (97:3) as eluent to give homogeneous fractions of the methylthio intermediate compound.

EXAMPLE 8

A solution of the methylthio compound of Example 7 (0.358 g, 0.85 mmole) in 100 ml of MeOH that has been saturated with NH$_3$ at 0° C. is heated at 90°-95° C. for 24 hours in a glass-lined stainless steel bomb. The contents of the chilled bomb are evaporated in vacuo to give a mixture of the desired 2-amino intermediate compound, benzamide, and a by-product that is a 2-methylthio derivative, as opposed to the 2-amino compound. The mixture is dissolved in methanol and the solution is evaporated with silica gel (about 5 g). The mixture is then carefully layered onto the top of a silica-gel chromatography column, which is then eluted with CHCl$_3$/MeOH (9:1) to give the methylthio by-product and the desired 2-amino-7-(3-pyridinylmethyl)-3H,5H-pyrrolo[3,2-d]pyrimidin-4-one, compound (IA). Further purification is obtained by recrystallization from boiling isopropyl acetate in a Soxhlet apparatus.

EXAMPLE 9

The compound (IA) of Example 8 is tested for enzyme inhibition activity. A purine nucleoside phosphorylase (PNP) enzyme assay is performed in which PNP activity (IC$_{50}$) for the compound is observed, which is determined radiochemically by measuring the formation of [$^{14}$C]-hypoxanthine from [$^{14}$C]-inosine (see *Biomedicine*, 33, 39 (1980) using calf spleen as the enzyme source.

EXAMPLES 10-14

The following compounds of the present invention are prepared that are 2-amino-7-(substituted methyl)-3H,5H-pyrrolo[3,2-d]pyrimidin-4-ones wherein substituted methyl is —CH$_2$R in which the R group is as follows:

| Example 10 | R = 2-methyl-3-pyridinyl |
|---|---|
| Example 11 | R = 2-chloro-3-pyridinyl |
| Example 12 | R = 2-trifluoromethyl-3-pyridinyl |
| Example 13 | R = 2-methoxy-3-pyridinyl |
| Example 14 | R = 2-fluoro-3-pyridinyl |

The compounds are prepared following the procedures set forth in Examples 1-8 using the appropriate 3-(pyridinyl)-propionitriles as starting materials.

EXAMPLES 15-20

The following compounds of the present invention are prepared that are 2-amino-7-(substituted methyl)-3H,5H-pyrrolo[3,2-d]pyrimidin-4-ones wherein substituted methyl is —CH$_2$-R in which the R group is as follows:

| Example 15 | R = 2-pyridinyl |
|---|---|
| Example 16 | R = 4-pyridinyl |
| Example 17 | R = 3-chloro-2-pyridinyl |
| Example 18 | R = 3-trifluoromethyl-4-pyridinyl |
| Example 19 | R = 3-methoxy-4-pyridinyl |
| Example 20 | R = 3-fluoro-2-pyridinyl |

The compounds are prepared following the procedures set forth in Examples 1-8 using the appropriate 3-(pyridinyl)-propionitriles as starting materials.

EXAMPLE 21

A pharmaceutical composition for intraperitoneal injection is prepared for testing the compound (IA). An intraperitoneal injection solution containing the compound of Example 8 is dissolved in an aqueous carrier that contains ten percent DMSO.

EXAMPLE 22

The compound (IA) is intraperitoneally injected into Lewis Rats via the test composition of Example 21 to provide 30 mg of the compound (IA), with an injection given twice per day. Controls are used, which receive only the vehicle. At specific times after administration, the animals are sacrificed and plasma samples are prepared. The plasma is extracted with cold 0.5N HClO$_4$ and neutralized with solid NH$_4$HCO$_3$. After removal of perchlorate salts, the extract is subjected to HPLC on a reversed phase column (Spherisorb ODSI). A significant increase in plasma inosine is observed in the plasma taken from animals receiving the compound (IA).

EXAMPLES 23-33

Compounds prepared as in Examples 10-20 are each made into a pharmaceutical formulation in accordance with the preparation of Example 21 and the resultant injectable solutions are tested in accordance with the procedure of Example 22. A significant increase in plasma inosine is observed in the plasma taken from animals receiving the compounds of the present invention.

What is claimed is:

1. A compound of the formula 2-amino-7-(substituted methyl)-3H,5H-pyrrolo[3,2-d]pyrimidin-4-one wherein substituted methyl is —$CH_2$-R wherein R is pyridinyl optionally substituted by halogen, hydroxy, alkoxy, alkyl or trifluoromethyl.

2. The compound of claim 1 wherein R is 2-pyridinyl.
3. The compound of claim 1 wherein R is 3-pyridinyl.
4. The compound of claim 1 wherein R is 4-pyridinyl.
5. The compound of claim 1 wherein R has at least one substituent selected from the group consisting of chloro, feluoro, methoxy, ethoxy, propoxy, butoxy, methyl, ethyl, propyl and butyl.

6. A method for the selective suppression of mammalian T-cell function without diminished effect on humoral immunity which comprises administering to a mammal the compound of claim 1, whereby said compound inhibits purine nucleoside phosphorylase and thereby T-cell formation.

7. A method for the selective suppression of mammalian T-cell function without diminished effect on humoral immunity which comprises administering to a mammal the compound of claim 5, whereby said compound inhibits purine nucleoside phosphorylase and thereby T-cell formation.

8. A pharmaceutical composition for the selective suppression of mammalian T-cell function without diminished effect on humoral immunity which comprises an effective amount of the compound of claim 1 capable of said selective suppression and a pharmaceutically acceptable carrier or diluent therefor.

9. A pharmaceutical composition for the selective suppression of mammalian T-cell function without diminished effect on humoral immunity which comprises an effective amount of the compound of claim 5 capable of said selective suppression and a pharmaceutically acceptable carrier or diluent therefor.

* * * * *